United States Patent [19]
Hakimi

[11] Patent Number: 5,915,385
[45] Date of Patent: Jun. 29, 1999

[54] SNORE AND STRESS RELIEVING DEVICE

[76] Inventor: Farhad Hakimi, 1185 Park Ave. Apartment 15K, New York, N.Y. 10128

[21] Appl. No.: 08/828,910

[22] Filed: Apr. 2, 1997

[51] Int. Cl.⁶ ........................................................ A61F 5/56
[52] U.S. Cl. ............................ 128/848; 128/859; 602/902
[58] Field of Search .................................... 128/848, 846, 128/859–862; 602/902

[56] References Cited

U.S. PATENT DOCUMENTS

| | | | |
|---|---|---|---|
| 746,869 | 8/1903 | Moulton . | |
| 1,674,336 | 6/1928 | King . | |
| 2,424,533 | 7/1947 | Faires | 128/136 |
| 2,521,039 | 9/1950 | Carpenter | 128/136 |
| 2,590,118 | 3/1952 | Oddo, Jr. | 128/136 |
| 2,882,893 | 4/1959 | Godfroy | 128/861 |
| 3,132,647 | 5/1964 | Corniello | 128/136 |
| 3,434,470 | 3/1969 | Strickland | 128/136 |
| 3,457,916 | 7/1969 | Wolicki | 128/136 |
| 3,871,370 | 3/1975 | McDonald | 128/136 |
| 4,304,227 | 12/1981 | Samelson | 128/136 |
| 4,495,945 | 1/1985 | Liegner | 128/200.26 |
| 4,568,280 | 2/1986 | Ahlin | 433/6 |
| 4,593,686 | 6/1986 | Lloyd et al. | 128/136 |
| 5,056,534 | 10/1991 | Wright | 128/848 |
| 5,092,346 | 3/1992 | Hays et al. | 128/848 |
| 5,117,816 | 6/1992 | Shapiro | 128/861 |
| 5,277,202 | 1/1994 | Hays | 128/848 |
| 5,316,020 | 5/1994 | Truffer | 128/861 |
| 5,427,117 | 6/1995 | Thornton | 128/848 |
| 5,792,067 | 8/1998 | Karell | 128/848 |

FOREIGN PATENT DOCUMENTS

| | | | |
|---|---|---|---|
| 599445A1 | 6/1994 | European Pat. Off. | A61F 5/56 |
| 2320501 | 11/1974 | Germany | A61F 5/56 |
| 1569129 | 6/1980 | United Kingdom | A61F 5/56 |

OTHER PUBLICATIONS

E. H. Williamson & J.W. Sheffield, *The Treatment of Internal Derangement of the Temporomandibular Joint: A Survey of 300 Cases*, The Journal of Craniomandibular Practice, Apr. 1987 V. 5, No. 2.

G. T. Clark & M. Nakano, *Dental Appliance for the Treatment of Obstructive Sleep Apnea*, Journal of the Dental Association, May 1989 V. 118.

D.P. Dennis, *Snoring (Called in Extreme Cases Sleep Apnea)*, Atlanta Center for Ear, Nose and Throat, Mar. 1997.

*Primary Examiner*—Michael A. Brown
*Attorney, Agent, or Firm*—Sofer & Haroun, LLP

[57] ABSTRACT

A dental device for removable placement in the mouth of a user for eliminating snoring and relieving stress. The device includes and upper member which is adapted for engagement with the user's upper dentition. An anterior extension suspends downwardly from the upper member and includes an interior surface and an exterior surface. The exterior surface is configured based on the user's jaw and mouth anatomy so that the exterior surface engages at least some of the lower front teeth in the user's mouth. Engagement of the exterior surface of the anterior extension with the user's lower front teeth advances the user's jaw forward with respect to the user's upper jaw such that the user's upper airway is enlarged and the passage of air though the upper airway is facilitated. The interior surface of the anterior extension is advantageously provided with a rough texture for attracting and positioning the tongue in a forward position. The upper member also includes a support member which lies proximate the hard palate in the user's mouth and has a rearwardly extending posterior portion configured to engage the soft palate of the user to complement the forward advancement of the user's lower jaw and open the user's upper airway to reduce vibration of the soft tissues in the upper airway which cause snoring.

25 Claims, 2 Drawing Sheets

SNORE AND STRESS RELIEVING DEVICE

FIELD OF THE INVENTION

This invention relates to a device for relieving stress and reducing snoring, and in particular, to a dental orthosis for easy engagement with the upper dentition of a user and intended to eliminate snoring and alleviate temporomandibular stress disorders.

BACKGROUND OF THE INVENTION

Snoring is the sound of soft tissues in the back of the mouth striking against each other and vibrating while one sleeps. The unpleasant snoring sounds are produced as a result of narrowing and partial obstruction of the upper airway at this site. Snoring is one of life's little annoyances, especially to one's bedmate. The familiar noise is the butt of countless jokes and a favorite sound effect for Saturday morning cartoons on television. But snoring can also be a serious medical problem.

In its most extreme form it is called obstructive sleep apnea and can be a signal of more serious problems that can lead to fatigue, high blood pressure, stroke, irregular heartbeat and irreversible heart disease. The commonly known snoring sounds have been traced to a number of soft tissues in the back of the mouth and throat, namely, the uvula, a fleshy tab visible at the rear of the mouth; the soft palate, the flesh that separates the roof of the mouth from the nasal cavity; the tongue; and the tonsils and adenoids. When a person is awake, there is no problem. However, while asleep in a supine position, muscles relax, and the tissues, unsupported by the nearby bone structure, collapse into the upper airway making the airway smaller. This decrease in the airway space increases the velocity of air flowing through the airway during breathing. As the velocity of required air is increased in the constricted space, soft tissues like the uvula and the soft palate vibrate. These vibrations of the soft tissues in the mouth and throat result in what is called "noisy breathing" or generally referred to as snoring.

Other than sleep disturbance and the social consequences stemming from the unpleasant snoring sounds, breathing generally may become abnormal and impaired as a result of the narrow and partially obstructed upper airway. Snoring has also been associated with the obstructive sleep apnea syndrome, a serious condition characterized by periodic obstruction of the upper airway which most often occurs in persons who sleep in the supine position. Persons suffering from obstructive sleep apnea syndrome often experience choking and gasping which require arousal from sleep in order to relief the obstructed air way and breath normally.

Surgical techniques to remove obstructions in the uvula, soft palate, enlarged tonsils and adenoids have been among the many attempted snoring remedies. These soft tissue surgical procedures have shown only moderate success rates (e.g. 20% to 40%). In addition to only moderate success in correcting snoring conditions, surgical correction of snoring conditions are also extremely expensive, often require many days of post-operative recovery, and which generally leave the patient with substantial discomfort and pain.

As an alternative to surgery, oral devices or dental orthosises have been developed to eliminate snoring. These devices are generally affordable, non-invasive and comfortable in use. Research has shown that custom fabricated dental devices worn at night which move the lower jaw into a forward position, increase the three dimensional space in the airway tube which reduces air velocity and soft tissue vibration. By increasing the volumetric capacity of the airway and preventing soft tissue vibrations, snoring is substantially eliminated.

Various snore and stress reducing devices are known in the art and represented by U.S. Pat. Nos. 746,869, 1,674,336, 2,424,533, 3,132,647, 3,434,470, 4,304,227, 4,568,280, 5,092,346, 5,117,816, 5,277,202 and 5,427,117. Each of these known prior art devices are directed to preventing snoring, sleep apnea, and/or relieving stress caused by temporomandibular disorders by concentrating on only one part of the problem. For example, U.S. Pat. Nos. 746,869, 2,424,533, 3,434,470, 4,304,227, and 5,956,534 provide mouthpiece devices directed to regulating the ingress and egress of air inhaled and exhaled through the mouth. As previously explained, by attempting to control the quantity of air inhaled and exhaled, the vibration of the uvula and soft palate incident to snoring may be alleviated. These devices, however, rely to a great deal on the user's ability to breath through their nose. However, a patient will not be able to effectively use these devices if he/she is unable to breathe through the nose.

Other devices such as that disclosed in U.S. Pat. No. 5,427,117, is directed to a two-piece device comprising an upper arch fitted to the upper dentition and a lower arch fitted to the lower dentition. A post extends from the upper arch and contacts the lower arch so as to extend the user's jaw forward to open the user's airway and reduce the vibrations which result in snoring. This arrangement is, however, extremely uncomfortable since it is fitted to both the upper and lower dentition, which fixes their relative positions, inhibits natural mouth motions, and oftentimes leads to abrasions of the gums and inner cheeks of the user's mouth.

Another prior art arrangement for reducing snoring is exemplified by the device of U.S. Pat. No. 3,132,647 to Corniello. Corniello intends that his device will prevent snoring in the user by insuring an adequate air passage between the base of the tongue and the soft palate and that such a free air passage may be provided by depressing the rear portion of the tongue. His structure comprises a member adapted for engagement with a user's upper teeth and including means extending downward from the rear of the member to contact and depress the user's tongue. This device, has not found widespread use since many user's find the depression of the tongue to be irritating and uncomfortable.

U.S. Pat. No. 1,674,336 to King teaches another device for reducing snoring by maintaining a plentiful supply of oxygen to the blood of a user during sleep. King's structure comprises an upper channel and a lower channel to receive the upper and lower teeth, respectively. The two channels are spaced apart to prop the upper and lower front teeth apart and to create an air passage therebetween. Therefore, the device props the teeth of the user apart in a fixed position, which King claims opens the posterior airway to facilitate the passage of air to and from the throat and lungs. This, device however, is large and bulky, and places the teeth in a fixed position which thus prevents natural mouth movements and motion of the lower jaw.

U.S. Pat. Nos. 5,092,346, 5,277,202, 5,117,816 disclose anti-snoring devices which comprise upper elements adapted to be fitted upon the teeth of the upper dentition of the user. Each of these devices also include ramp or anterior portions which extend downward from the upper element and which engage some of the teeth of the lower dentition so as to cam or shift the lower jaw forward so as to provide an open airway and reduce snoring in the wearer. Although each of these devices engage only the upper dentition, the devices are large and occupy much of the area in the user's mouth. As such, the devices are provide with apertures or air chambers which extend through the device to permit the passage of air therethrough. Thus, although shifting the lower jaw forward opens the airways and reduces snoring, the size of the devices actually allow the passage of air into and out of the mouth only through relatively small apertures.

Accordingly, there is a need for an anti-snoring device which is small, lightweight, adaptable for removable engagement with the upper dentition of a user's mouth, and which is configured so as to provide easy and unobstructed breathing by the user.

OBJECTS AND SUMMARY OF THE INVENTION

It is thus a general object of the present invention to provide a dental orthosis for use in the prevention of snoring.

It is a more specific object of the present invention to provide a dental orthosis which is removably maintained upon the upper dentition of a user and which is configured to open the user's airway passage to provide for free and easy breathing of air through the user's mouth.

It is a further object of the present invention to provide an unobstructed airway to permit free breathing and to prevent vibration of the soft tissues in the mouth which result in snoring.

It is another object of the present invention to provide a dental orthosis which is easily moldable to the upper dentition of a user's mouth, which is comfortable to wear, and which permits natural movement of the lower jaw.

It is still a further object of the present invention to provide a dental orthosis which permits a forward shifting of the lower jaw and which places pressure upon the soft palate in order to create an open airway so as to prevent snoring.

It is an additional object of the present invention to provide a dental orthosis which comprises means for shifting and maintaining the lower dentition in a forward posture.

It is still an additional object of the present invention to provide a dental orthosis which provides means for attracting the tongue forward.

These and other objects of the invention are realized by providing a dental orthosis in the form of a unitary oral device comprising an upper member having front and rear ends, and upper and lower surface portions. The upper member is generally u-shaped and includes inner and outer walls which extend upwardly from the upper surface portion to form a channel into which a user's upper dentition are engaged when the device is positioned within a user's mouth. An anterior extension is connected to the front end of the upper member and is suspended downward to engage at least some of the lower front teeth. A posterior portion is connected to the upper member, preferably at its rear end, and is arched upward and extends in a direction backwards and away from the upper member. The upper member is generally fabricated from a transparent heat-curing acrylic resin comprised of methylmethacrylate and a polymer. This composition renders the upper member capable of being custom fitted to adapt to the upper teeth of user's of varying ages.

When the anterior extension which suspends downward from the front end of the upper member engages the lower front teeth, the lower jaw is shifted or urged forward relative to the upper jaw and is properly positioned by engaging the interior surface of at least some of the teeth of the lower dentition. The interior surface of the anterior extension is advantageously rough in texture so as to attract and maintain the tongue in a forward position.

The posterior portion is also connected to the upper member and extends backwards towards a user's throat. The posterior portion arches upward from the upper member so that it engages and lifts the soft palate within the user's mouth when the device is properly positioned.

The shifting or urging forward of the lower jaw in combination with the raising of the soft palate causes the breathing airway to open wide enough to prevent vibration of the uvula and soft palate which results in snoring and the resultant unpleasant sounds.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

DETAILED DESCRIPTION OF THE DRAWINGS

In the drawings in which like reference characters denote similar elements throughout the several views.

DETAILED DESCRIPTION OF THE PRESENTLY PREFERRED EMBODIMENT

Figure 1:
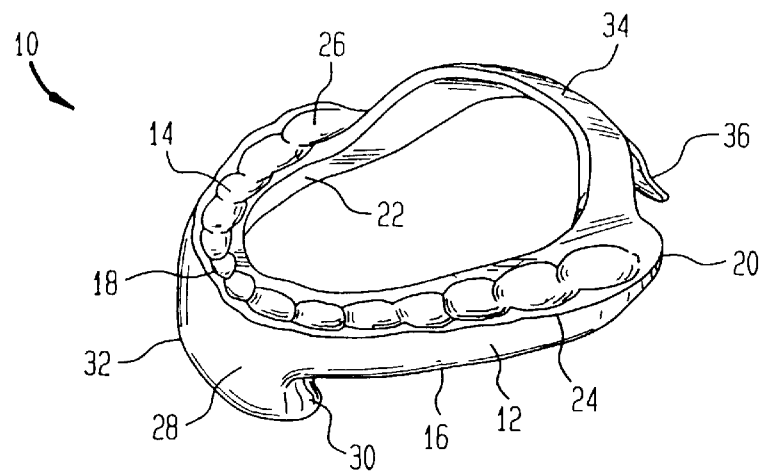
FIG. 1 illustrates a perspective view from the forward side of the snore and stress relieving device in accordance with one embodiment of the present invention.

The snore and stress relieving device, according to a preferred embodiment of the invention, shall now be described with initial reference to FIGS. 1–3. As shown therein, the snore and stress relieving device 10 comprises an upper member 12 advantageously configured as a u-shaped mouthpiece for engaging at least some of the teeth of the upper dentition of a patient or user (not shown). In the preferred embodiment illustrated in FIGS. 1–3, the entire device 10 is formed from a resilient thermoplastic material comprised of a transparent heat-curing acrylic resin, such as methylmethacrylate and a polymer.

Upper member 12 is provided with upper and lower surface portions 14 and 16, respectively. Upper member 12 also includes front and rear ends 18 and 20, respectively, and an anterior extension 28 advantageously attached to upper member 12 at front end 18. Inner and outer wall portions 22 and 24 respectively, extend upwardly from inner and outer edges of upper surface portion 14. Inner and outer wall portions 22, 24 extend rearward from front end 18 of upper member 12 towards the rear of a user's upper dentition. A channel 26 is defined between inner and outer wall portions 22, 24 and is generally custom formed for the receipt of at least some of the teeth of the upper dentition. Depending upon the size of the mouth of the user, the distance between inner and outer wall portions 22, 24 may be varied, e.g. for use of device 10 in a child's mouth, the distance between inner and outer wall portions 22, 24 will be small in contrast to a device for use by an adult with larger teeth. By filling channel 26 with another resin such as a fast-setting acrylic resin, upper member 12 may be custom fitted to a user's upper dentition. To this end, the teeth of the user's upper dentition are impressed into the resin which fills channel 26, such that an impression of the user's upper teeth is formed in the resin wherein upper member 12 is capable of being releasably secured to the user's upper dentition when properly positioned thereon.

Figure 2:
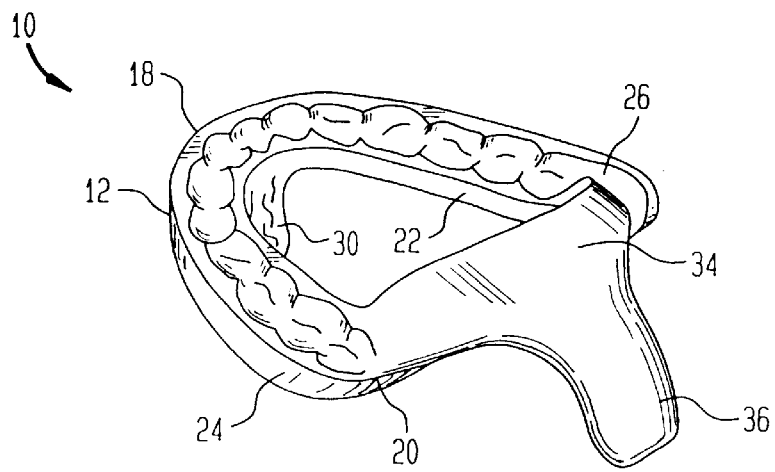
FIG. 2 illustrates a perspective view from the rear side of the snore and stress relieving device in accordance with one embodiment of the present invention.
Figure 3:
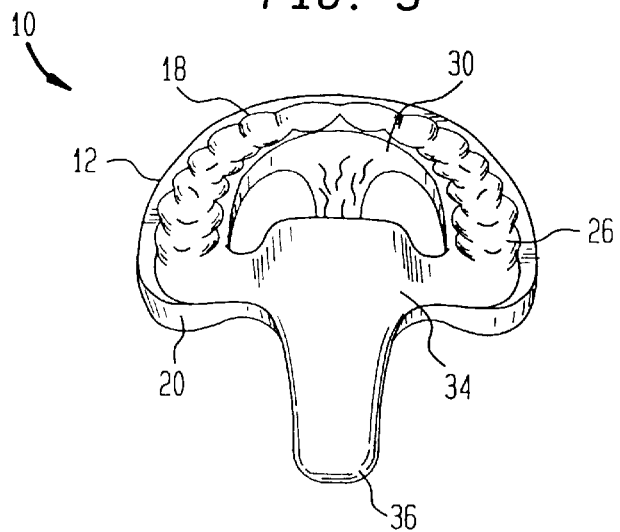
FIG. 3 illustrates a rear elevation view of the snore and stress relieving device in accordance with one embodiment of the present invention.

As further illustrated in FIGS. 1–3, upper member 12 includes an anterior extension 28 advantageously attached at front end 18. It is noted that anterior extension 28 may be uniformly molded with upper member 12 in accordance with one embodiment of the invention. Anterior extension 28 suspends downward from front end 18 of upper member 12 and varies in size and thickness according the user to which device 10 is fitted. Anterior extension 28 comprises an interior surface 30 and an exterior surface 32.

Figure 5:
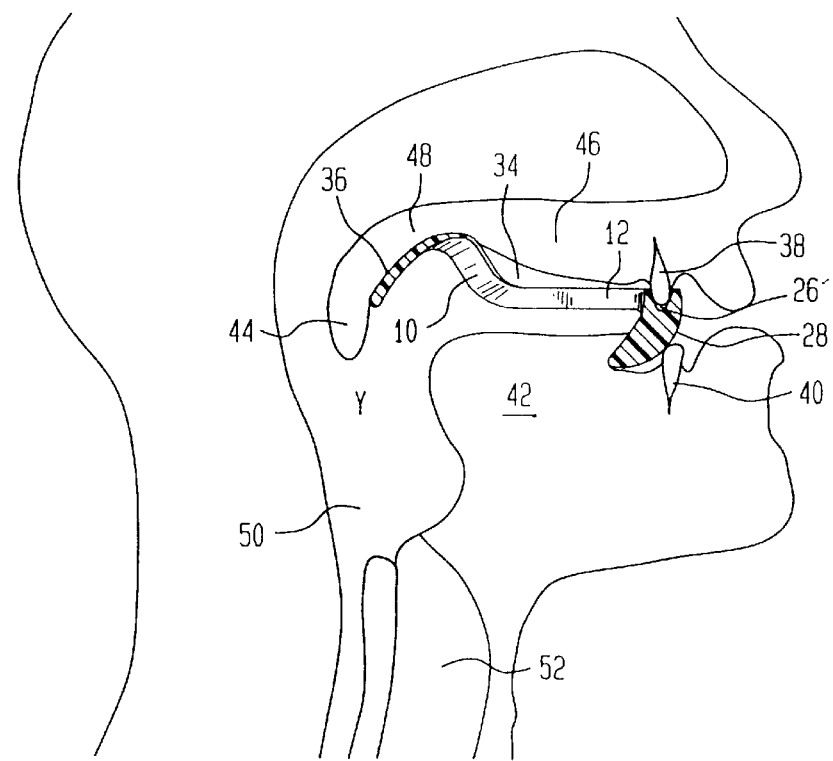
FIG. 5 illustrates a partial elevation in cross section of a human head and neck of FIG. 4 illustrating the snore and stress relieving device properly positioned within the mouth.

During the fitting of device 10, discussed in detail hereinbelow, exterior surface 32 of anterior portion 28 is configured so as to conform to the interior (lingual surface) of the front teeth of the lower dentition. Based on examination of user's jaw by a dental professional, anterior portion 28 is also custom configured to be of a predetermined thickness, such that when device 10 is properly inserted and fitted within a user's mouth, anterior extension 28 engages the user's lower dentition so as to maintain a forward posture of the user's lower jaw relative to the upper jaw, as shown in FIG. 5, such that the volumetric capacity of the user's upper airway is increased so as to alleviate snoring. For maximum comfort, exterior surface 32 of anterior portion is preferably formed to provide a smooth surface to prevent abrading of the user's gums and mouth tissues when exterior surface 32 of anterior portion 28 is properly positioned in the user's mouth.

Interior surface 30 is advantageously provided with a rough texture. When properly positioned upon a user's upper dentition, the rough texture of interior surface 30 of anterior extension 28 attracts the user's tongue and maintains the tongue in a forward position by creating a frictional attraction between the tongue and interior surface 30 of anterior extension 28. The positioning of the tongue in a forward position increases its distance between the uvula and soft palate and the tongue. As such, the forward positioning of the user's tongue complements the shifting of the user's jaw outward relative to the user's upper jaw and assists in increasing the volumetric capacity of the user's upper airway so as to reduce vibration of the uvula and soft palate which cause snoring.

Interior surface 30 of anterior extension 28 may also be provided with a bioadhesive material to assist in retaining the tongue in the forward position while the user is asleep. The bioadhesive material is advantageously Carbopal™, manufactured by B. F. Goodrich Corp. This material easily adheres to the acrylic resin of which upper member 12 is composed, it is non-toxic and is compatible with the pH level of the oral cavity. Furthermore, the presence or lack of saliva in the user's mouth does not affect or influence the materials adhesive properties. The invention is not limited, however, to the use of Carbopal™, and other bioadhesive material will be equally effective. The bioadhesive material may also be provided in a variety of flavors to provide a pleasant taste in the use's mouth. Furthermore, the bioadhesive material may include a mouth refreshing material which provides a refreshing taste in the user's mouth.

Anterior portion 28 is preferably of triangular configuration. Since anterior portion 28 serves to shift or urge the user's lower jaw outward, the size, shape and thickness of the triangular shaped anterior portion 28 is determined by the anatomy of the user's lower dentition and jaw structure, as well as the user's natural jaw movement. Additionally, the anatomy of the user's jaw structure determines the angle or slope of inclination of anterior portion 28. In general, the greater the outward shift of the user's jaw, the greater the slope of inclination of anterior portion 28. It is to be understood that the anterior portion 28 is not limited to a triangular configuration and other shapes and sizes may be more effective in certain users.

As shown in FIGS. 1–3, upper member 12 further comprises a support member 34 connected to upper member 12. When device 10 is fitted upon the teeth of the user's upper dentition, support member 34 is positioned proximate the hard palate of the user's mouth. A posterior portion 36 is attached to support member 34 and is directed rearwardly towards a user's throat, such that posterior portion 36 engages the user's soft palate. Engagement of posterior portion 36 with the user's soft palate assists in increasing the volumetric capacity of the user's airway.

In addition to upper member 12 and anterior portion 28, posterior portion 36 is also custom fitted within the user's mouth to provide for optimal engagement with the user's soft palate. Depending upon the anatomy of the user's mouth, posterior portion 36 may also be configured to arch upwardly so as to lift the user's soft palate slightly. Although FIGS. 1–3 illustrates support member as attached to upper member 12 at rear end 20, the invention is not limited in this respect. For example, posterior portion 36 may be extended and supported by any other location on upper member 12.

For optimal fitting and proper placement within a user's mouth, fabrication of device 10 is advantageously performed in dental laboratories by skilled technicians who operate from an impression made by the clinician who is treating the user. Device 10 may alternatively be fabricated and fitted by a dental professional within the dentist's office without the need for sending the mold or cast to a dental laboratory.

In one embodiment of the invention, the device 10 may be initially obtained from a one-size dental orthosis. Although mouth and dentition shapes and sizes vary considerably, a one-size dental orthosis is initially molded to be of such size and shape as to be capable of deformation to conform with most mouths with minimal further fitting. The one-size dental orthosis may easily trimmed with a scissor or other cutting implement to provide for an optimum fit. In general, the material of which device 10 is formed, in accordance with this embodiment, obtains a soft moldable form when heated to the temperature of boiling water, but reverts to a pliant yet firm form on cooling. Thus, device 10 can be molded in situ to conform to the user's upper dentition, soft palate and lower jaw configurations.

By positioning the user's upper teeth within channel 26 of upper member 12, posterior portion 24 is formed by pressing the resin against the user's upper palate. Anterior portion 28 is then configured with the proper thickness and including an angle or slope of inclination to provide the optimal forward shift for urging the lower jaw outward. After forming and fitting, device 10 is removed from the user's mouth to permit drying and hardening. Minor adjustments to the shape and form of the device may then be easily made by cutting and trimming necessary portions.

Device 10 may also be marketed to dental professionals in a package which contains a variety of pre-formed devices which may then be fitted to the user's upper dentition and custom sized for optimum fit. To provide for the varying mouth shapes and sizes, dental professionals may purchase packages provided with two or three devices 10 consisting of upper members 12 of different sizes, e.g. small and large. A deformable resin such as a fast-setting acrylic resin is then filled within channel 26 so that the engagement of the user's upper dentition within the resin forms an impression of the user's upper dentition to provide for a custom fit. After the resin hardens, the dental professional proceeds to form device 10 to further conform to the user's mouth by cutting and trimming any necessary portions of device 10. For example, children of different ages generally have different numbers of teeth. As such, in order to properly fit device 10 to a child, rear end 20 of upper member 12 may need to be trimmed or cut away to provide the proper size for engaging the teeth of the child's upper dentition.

Figure 4:
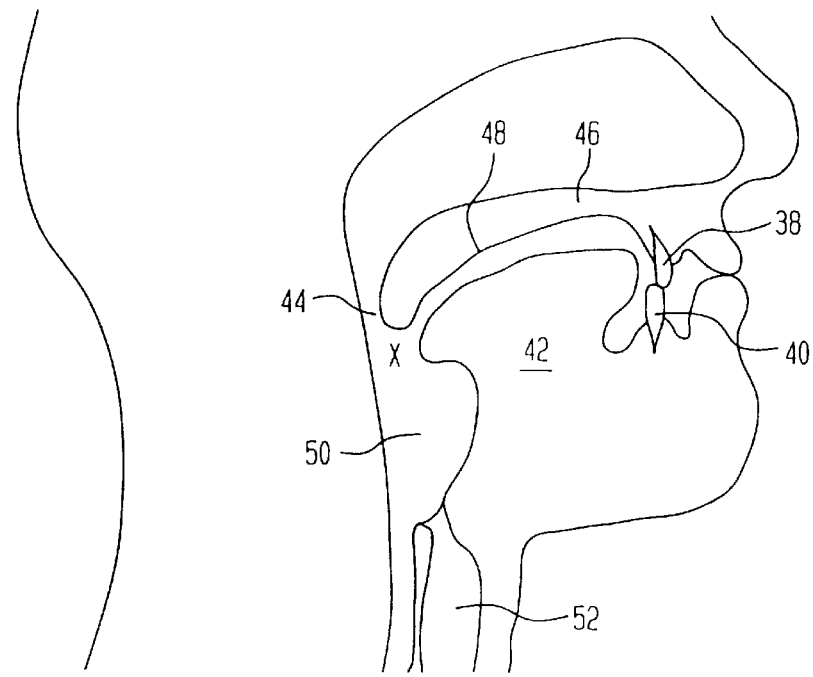
FIG. 4 illustrates a partial elevation in cross section of a human head and neck illustrating the internal anatomy of the mouth and throat.

FIGS. 4 and 5 illustrate the upper and lower dentition, jaw position and soft tissues of the mouth. FIG. 4. shows the normal dentition and jaw positioning of an average person. It can be seen that in this normal positioning, the teeth of the upper dentition 38 and the lower dentition 40 form an "overbite" arrangement. FIG. 4 also illustrates the natural positioning of the tongue 42, uvula 44, hard palate 46 and soft palate 48. As shown, soft palate 48 extends rearwardly and terminates in the uvula 44. The normal spacing of the opening to the airway 50 defined between the soft palate 48, the uvula 44 and the tongue 42 is indicated as X. The opening to upper airway 50 leads to the trachea 52 which is directed towards the lungs (not shown).

FIG. 5 illustrates the preferred embodiment device 10 in situ. As shown, the teeth of the upper dentition 38 are positioned within channel 26 of upper member 12. When the user's mouth closes naturally, as when asleep, anterior extension 28 engages the teeth of the lower dentition 40. As a result of the slope of inclination of exterior surface 32 of anterior extension 28, the engagement of the anterior portion against the teeth of the user's lower dentition shift or advance the user's jaw forward relative to the upper jaw. Furthermore, device 10 spaces the upper dentition from the lower dentition to allow easy inhalation and exhalation of air.

With continued reference to FIG. 5, support member 34 is shown in position proximate hard palate 46 and with posterior extension 36 engaging soft palate 48. The result of the combined engagements of anterior extension 28 against the teeth of the user's lower dentition 40, the forward positioning of the user's tongue 42 upon the rough textured interior surface 30 of anterior portion 28, and the engagement of posterior portion 36 upon the user's soft palate 48, increases the spacing at the opening (indicated as Y) of the upper airway 50 and reduces air velocity and vibrations of the soft tissues. Hence, by increasing the volumetric capacity of the upper airway and preventing soft tissue vibration, snoring is substantially reduced or eliminated.

When device 10 has been properly fitted, upper member 12 securely adheres to the user's upper dentition when properly inserted and positioned. Posterior portion 36 engages and exerts a slight lift upon the user's upper palate, which provides no discomfort to the user. When the user lies down in bed in a supine position the lower jaw exists in an unstressed position, such that the anterior portion 28 naturally engages the interior surface of the user's lower dentition. The engagement of the user's lower teeth with the sloped anterior portion 28 induces the lower jaw to extend forward relative to the upper jaw. While anterior portion 28 engages the user's lower dentition, the user's tongue is attracted to the rough surface of interior surface 30 of anterior extension 28 which, as discussed previously may be provided with a bioadhesive material to assist in retaining the tongue in a forward position such that the distance between the tongue and the uvula and soft palate is increases. This maintenance of the user's tongue in a forward position further increases the opening of the upper airway to facilitate breathing and reduce vibration of the uvula and soft palate which causes snoring.

By shifting or urging the lower jaw forward, lifting the soft palate, and spacing the upper and lower teeth, the lower dentition extends forwardly beyond the upper dentition while the user is asleep, such that the spacing of the user's breathing airway is enlarged between the tongue and soft palate and uvula. The enlargement of the breathing airway reduces the velocity of air which is inhaled and exhaled, and significantly and oftentimes completely eliminates the vibrations of the soft palate and uvula thereby reducing or eliminating the "noisy breathing" which resulted from these vibrations.

Although the above-described device is adapted for and directed to the reduction and elimination of snoring and the prevention of obstructive sleep apnea. Device 10 also functions as a stress reducing device by relieving pressure on the temporomandibular joint. As a stress relieving device anterior portion 32 is advantageously triangular in shape but smaller in size than the anterior portion 32 used for the purpose of preventing snoring. As such, only a few of the user's lower front teeth contact anterior portion 32. For stress relief function, support member 34 and posterior portion 36 are eliminated. For relieving stress, the objective of device 10 is to separate the upper and lower dentition and shift the lower jaw slightly forward, hence the smaller size of anterior portion 32. As a result of the separation of the upper and lower dentition and the engagement of anterior portion 32 against the lower front teeth when the user's lower jaw is closed, pressure on the temporomandibular joint, teeth and internal parts of the ear, relieves muscle spasms.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirt of the invention. It is the intention, therefore, to be limited only as indicated by the scope of the claims appended hereto.

It is to be understood that the drawings are not necessarily drawn to scale, but that they are merely conceptual in nature.

What is claimed is:

1. A device for removable placement in the mouth of a user for eliminating snoring and relieving stress, comprising:

an upper member adapted to be engaged with the upper dentition of a user;

an anterior extension suspended downwardly from said upper member, said anterior extension configured to be engaged against at least some of the lower front teeth of the lower dentition in said user's mouth, wherein engagement of said anterior extension with the lower front teeth causes the jaw of said user to be advanced forward, said anterior extension configured to position said user's tongue in a forward position; and a support member connected to said upper member, said support member having a rearwardly extending posterior portion configured to exert pressure on the soft palate of a user's mouth so as to increase the volumetric capacity of the user's airway to facilitate said user's breathing and reduce snoring.

2. The device as recited in claim 1, wherein said upper member further comprises front and rear ends, and upper and lower surface portions.

3. The device as recited in claim 2, wherein said upper member further comprises inner and outer upstanding wall portions extending upwardly from said upper surface portion to define a channel for receiving at least a portion of at least some teeth of the upper dentition in said user's mouth.

4. The device as recited in claim 2, wherein said anterior extension suspends downwardly from said front end of said upper member.

5. The device as recited in claim 1, wherein said anterior extension further comprises an interior surface and an exterior surface.

6. The device as recited in claim 5, wherein said interior surface of said anterior extension is provided with a rough texture for attracting and maintaining said user's tongue in a forward position.

7. The device as recited in claim 6, wherein said interior surface of said anterior extension is provided with a bioadhesive material to retain the tongue thereto in a forward position.

8. The device as recited in claim 7, wherein said bioadhesive material is flavored.

9. The device as recited in claim 1, wherein said anterior extension is triangular in shape.

10. The device as recited in claim 1, wherein the slope of said anterior extension is adjusted according to the distance said user's lower jaw is to be advanced forward.

11. The device as recited in claim 1, wherein said support member engages the hard palate of said user.

12. The device as recited in claim 1, wherein said posterior portion is configured to lift said soft palate to increase spacing in the upper airway to facilitate breathing.

13. A device for removable placement in the mouth of a user for eliminating snoring and relieving stress, comprising:

an upper member adapted to be engaged with the upper dentition of a user; and an anterior extension suspended downwardly from said upper member, said anterior extension having an interior surface and an exterior surface, said exterior surface configured to be engaged against at least some of the lower front teeth of the lower dentition in said user's mouth, wherein engagement of said anterior extension with the lower front teeth causes the jaw of said user to be advanced forward, said interior surface of said anterior extension including a surface having a rough texture and configured to attract and maintain said user's tongue in a forward position.

14. The device as recited in claim 13, wherein said upper member further comprises front and rear ends, and upper and lower surface portions.

15. The device as recited in claim 14, wherein said upper member further comprises inner and outer upstanding wall portions extending upwardly from said upper surface portion to define a channel for receiving at least a portion of at least some teeth of the upper dentition in said user's mouth.

16. The device as recited in claim 14, wherein said anterior extension suspends downwardly from said front end of said upper member.

17. The device as recited in claim 13, wherein said interior surface of said anterior extension is provided with a bioadhesive material to retain the tongue thereto in a forward position.

18. The device as recited in claim 13, wherein said exterior surface of said anterior extension further comprises is an angle of inclination which is adjustable according to the distance said user's lower jaw is to be advanced forward.

19. A device for removable placement in the mouth of a user for eliminating snoring and relieving stress, comprising:

an upper member having front and rear ends, and upper and lower surface portions adapted to be engaged with the upper dentition of a user; and a support member connected to said upper member, said support member having a rearwardly extending posterior portion configured to exert pressure on the soft palate of a user's mouth so as to increase the volumetric capacity of the user's airway to facilitate said user's breathing and reduce snoring.

20. The device as recited in claim 19, wherein said support member engages the hard palate of said user.

21. The device as recited in claim 19, wherein said posterior portion is configured to lift said soft palate to increase spacing in the areas to facilitate breathing.

22. The device as recited in claim 19, wherein said upper member further comprises front and rear ends, and upper and lower surface portions.

23. The device as recited in claim 19, wherein said upper member further comprises inner and outer upstanding wall portions extending upwardly from said upper surface portion to define a channel for receiving at least a portion of at least some teeth of the upper dentition in said user's mouth.

24. A method of providing a device in a user's mouth for reducing snoring and relieving stress, which comprises the steps of:

inserting into said user's mouth said device comprising,
an upper member adapted to be engaged with the upper dentition of a user;

an anterior extension suspended downwardly from said upper member, said anterior extension configured to be engaged against at least some of the lower front teeth of the lower dentition in said user's mouth, wherein engagement of said anterior extension with the lower front teeth causes the jaw of said user to be advanced forward, said anterior extension configured to position said user's tongue in a forward position; and a support member connected to said upper member, said support member having a rearwardly extending posterior portion configured to exert pressure on the soft palate of a user's mouth;

positioning the teeth of said user's upper dentition so that said support member rests proximate said user's hard palate while said posterior portion exerts pressure on said soft palate, and said anterior portion engages at least some teeth of said user's lower dentition so as to advance said lower jaw forward with respect to said upper jaw, allowing the enlargement of said user's upper airway.

25. The method as recited in claim 24, wherein said anterior extension further comprises an interior surface and an exterior surface, said interior surface provided with a rough texture for attracting and maintaining said user's tongue in a forward position.

* * * * *